United States Patent
Chakravarthy et al.

(10) Patent No.: US 12,207,933 B1
(45) Date of Patent: Jan. 28, 2025

(54) DETECTOR FOR IDENTIFYING PHYSIOLOGICAL ARTIFACTS FROM PHYSIOLOGICAL SIGNALS AND METHOD

(71) Applicant: NeuroWave Systems Inc., Cleveland Heights, OH (US)

(72) Inventors: Niranjan Chakravarthy, Eden Prairie, MN (US); Stèphane Bibian, Cleveland Heights, OH (US); Tatjana Zikov, Cleveland Heights, OH (US)

(73) Assignee: NeuroWave Systems Inc., Cleveland, OH (US)

( * ) Notice: Subject to any disclaimer, the term of this patent is extended or adjusted under 35 U.S.C. 154(b) by 1058 days.

(21) Appl. No.: 17/144,277

(22) Filed: Jan. 8, 2021

Related U.S. Application Data

(63) Continuation of application No. 15/645,240, filed on Jul. 10, 2017, now abandoned.

(51) Int. Cl.
*A61B 5/369* (2021.01)
*A61B 5/00* (2006.01)

(52) U.S. Cl.
CPC ............ *A61B 5/369* (2021.01); *A61B 5/7203* (2013.01); *A61B 5/4094* (2013.01); *A61B 5/4812* (2013.01); *A61B 5/721* (2013.01); *A61B 5/7221* (2013.01)

(58) Field of Classification Search
CPC ..... A61B 5/369; A61B 5/7203; A61B 5/4094; A61B 5/4812; A61B 5/721; A61B 5/7221
See application file for complete search history.

(56) References Cited

U.S. PATENT DOCUMENTS

| | | | | |
|---|---|---|---|---|
| 3,807,387 | A * | 4/1974 | MacNichol, Jr. | A61B 5/369 600/544 |
| 6,032,072 | A * | 2/2000 | Greenwald | A61B 5/398 600/397 |
| 6,317,627 | B1 * | 11/2001 | Ennen | A61B 5/4821 600/545 |
| 2011/0245708 | A1 * | 10/2011 | Finkel | A61N 1/36071 600/544 |
| 2012/0083647 | A1 * | 4/2012 | Scheinin | A61N 5/0622 607/101 |
| 2012/0277548 | A1 * | 11/2012 | Burton | G01R 29/26 600/559 |

* cited by examiner

*Primary Examiner* — Jacqueline Cheng
*Assistant Examiner* — Tho Q Tran
(74) *Attorney, Agent, or Firm* — Brian Kolkowski

(57) ABSTRACT

The present invention relates to a physiological monitor and system, more particularly to an electroencephalogram (EEG) monitor and system, and a method of detecting the presence and absence of artifacts and possibly removing artifacts from an EEG, other physiological signal or sensor signal without corrupting or compromising the signal. The accurate and real-time detection of the presence or absence of artifacts and removal of artifacts in an EEG or other signal allows for increased reliability in the efficacy of those signals. The strategy of rejecting artifact-corrupted EEG can result in unacceptable data loss, and asking subjects to minimize movements in order to minimize artifacts is not always feasible. The present invention allows for increased accuracy in detection and removal of artifacts from physiological signals, substantially in real time, and without the loss or corruption of signal or data in order to increase the accuracy of such signals for diagnosis and treatment purposes.

20 Claims, 13 Drawing Sheets

DETECTOR FOR IDENTIFYING PHYSIOLOGICAL ARTIFACTS FROM PHYSIOLOGICAL SIGNALS AND METHOD

CROSS-REFERENCE TO RELATED APPLICATIONS

This application is a continuation of U.S. patent application Ser. No. 15/645,240, which was filed on Jul. 10, 2017 and which is a continuation of U.S. patent application Ser. No. 13/104,167, which was filed on May 10, 2011 and which claims priority to U.S. Provisional Patent Application Ser. No. 61/348,114, which was filed on May 25, 2010. The specifications and drawings of each of the above applications are hereby incorporated by reference in their entirety.

LICENSE RIGHTS-FEDERAL SPONSORED RESEARCH

The U.S. Government has a paid-up license in this invention and the right in limited circumstances to require the patent owner to license others on reasonable terms provided for by the terms of grant number R44NS-046978-02 awarded by the National Institute of Neurological Disorders and Stroke.

BACKGROUND OF THE INVENTION

1. Field of the Invention

The present invention relates to processing of signals, and particularly to the processing of electrophysiological signals. More particularly, the present invention relates to detection, identification and in some embodiments the removal of artifacts in biomedical signals including EEG signals. Further, the present invention relates to an automated method for identification and/or removal of artifacts from these signals.

2. Technology Review

Electroencephalograph (EEG) monitoring is a valuable non-invasive tool for monitoring brain activity. However, EEG signals are susceptible to various physiological artifacts such as ocular artifacts (eye blinks, rapid eye movements, etc.), muscle artifacts (head movement, biting, swallowing, facial movements, etc.), cortical activity artifacts (awake and sleep brain activity, etc.), as well as other, non-physiological artifacts (electrode or lead movement, percussion from an intravenous drip, etc.). These artifacts can seriously undermine EEG interpretation, especially in automated real-time analysis. The strategy of rejecting artifact-corrupted EEG can result in unacceptable data loss, while alternatively asking subjects to minimize movements in order to minimize artifacts is not always feasible. Hence, the automated detection and removal of artifacts is an important tool to develop.

Various methodologies have been proposed for EEG artifact detection and removal. Time domain and frequency domain regression methods are based on subtracting a portion of a recorded electrooculogram (EOG) from the EEG. These methods have an inherent drawback in that they do not take into account the propagation of EEG activity into the recorded EOG, which can lead to relevant portions of the EEG signal being cancelled along with the artifact. Moreover, these methods are heavily dependent on having a good regressing EOG channel. Furthermore, it is difficult to extend this to other artifacts such as those caused by physiological signals as well as artifacts caused by movement or sweating, since reference signals may not be available. EOG signals have also been used for ocular artifact minimization through adaptive filtering techniques. These techniques also require the availability of EOG reference signals.

Principal component analysis (PCA) is another technique used to remove ocular artifacts from multi-channel EEG. While it purportedly is more effective than regression or dipole model-based methods, PCA cannot completely separate ocular artifacts from either EEG when they are of comparable amplitudes or non-EOG based artifacts.

Independent component analysis (ICA) based methods also have been developed to overcome some of the above drawbacks and have shown some promise in removing a wide variety of artifacts. ICA methods linearly "unmix" multi-channel scalp EEG into independent components, and do not typically need reference channels corresponding to each artifact source. ICA methods are applicable to multi-channel EEG recordings and require visual inspection of the independent components to implement artifact removal, although automated artifact recognition and removal algorithms have recently been proposed.

In addition recently, wavelet-based artifact identification and removal methods have become popular since they do not require reference channels or multiple EEG channels for artifact removal, and are applicable in real-time.

These techniques and the devices using them are unable to detect artifacts in real time due to batch processing techniques for identifying the artifacts or due to computationally intensive techniques. Further oftentimes the removal of artifacts using these techniques can result in more questionable data resulting from false positive identification of artifacts or false negative failure of identification.

In addition to EEG monitoring, better techniques and devices using artifact removal methods are needed for many types of signal processing applications such as EEG, EOG, EMG, and ECG, for physiological and other signals based on the central or autonomous nervous system, for anesthesia monitoring, for seizure detection, for sedation monitoring and the like.

It is therefore an object of the present invention to provide a device, system, monitor and method that meets all of these needs and others where such a device and method would be applicable. It is another object of the present invention that this device and method detect and in some cases remove artifacts in real time. Finally it is an object of the present invention that a patient's diagnosis and therapeutic treatment be more accurately determined based on the better diagnostic data from the testing of the patient.

SUMMARY OF THE INVENTION

The present invention relates to a physiological monitor and system, more particularly to an electroencephalogram (EEG) monitor and system, and a method of detecting the presence and absence of artifacts and possibly removing artifacts from an EEG, other physiological signal or sensor signal without corrupting or compromising the signal.

The accurate and real-time detection of the presence or absence of artifacts and removal of artifacts in an EEG or other signal allows for increased reliability in the efficacy of those signals. The artifact removal methods of the present invention can be used in a variety of applications. For example, these methods can be used for artifact removal from most physiological signals including electrocardiogra electroencephalography (EEG), electrical impedance tomography (EIT), electromyography (EMG) and electro-oculography (EOG). These methods and the systems and devices using these methods preferably can be used for brain dysfunction or activity monitoring such as for anesthesia monitoring, for seizure detection, for sedation monitoring and the like. These methods and the systems and devices using these methods preferably can be used with equipment for the operating room, acute care such as the intensive care unit, critical care such as the emergency room, or in the field. These methods and the systems and devices using these methods can be used by anesthesiologists, nurse anesthetists, neurologists and neurosurgeons, pulmonologists, emergency room physicians and clinicians, intensive care physicians and clinicians, medics, paramedics, emergency medical technicians, respiratory technicians, and the like. Preferably, these methods and the systems and devices using these methods can be used by individuals or clinicians with little or no training in signal analysis or processing. These methods preferably are used with anesthesia monitors, seizure detectors, sedation monitors, sleep diagnostic monitors, any sort of ECG monitor, any sort of EEG monitor, battlefield monitors, operating room monitor, ICU monitor, emergency room monitor, and the like.

The various embodiments of the system of the present invention were developed for monitoring and processing various physiological signals from a subject. Preferably, this system is used for the brain wave or activity monitoring of a single patient or multiple patients. Preferably, the system is a multi-channel EEG system; however, depending on purpose of use and cost, systems may have as few as 1 channel. Preferably, the system or monitor of the present invention also includes one or more methods or algorithms for detecting or quantifying cortical activity, level of consciousness, sleep stage, seizure detection, level of sedation and the like. Preferably, the system or monitor can also measure muscle activity, EMG, contained in the EEG signal. In addition, the system and related methods can use other sensors that measure physiological or other sensor signals which directly or indirectly result in or from brain dysfunction, or effect or result from brain activity. In other embodiments, the system and related methods as adapted and set forth herein can use physiological and other sensor signals for measuring ECG, EOG, EMG, and other physiological signals known to those skilled in the art; or for measuring function or other aspects or a human or other animal body.

Preferably, the system or monitor is constructed to be rugged, so as to withstand transport, handling and use in all of the applications listed above including in emergency scenarios, such as on the battlefield or in mass casualty situations, or to reliably survive daily use by emergency medical personnel or other first responders. The system or monitor should preferably be splash-proof (or water tight), dust-tight, scratch-resistant, and resistant to mechanical shock and vibration. The system or monitor should preferably be portable and field-deployable in particular embodiments to a military theater of operation, the scene of an accident, the home of a patient, or to any clinical setting.

The system or monitor should preferably be designed for non-expert use. By this, it is meant that a person should not be required to possess extraordinary or special medical training in order to use the system effectively and reliably. The system should therefore preferably be automatic in operation in a number of respects. First, the system should be preferably capable of automatic calibration. Second, the system should preferably have automatic detection of input signal quality; for example, the system should be capable of detecting an imbalance in electrode impedance. Third, the system should preferably be capable of artifact detection and removal on one or more levels, so as to isolate for analysis that part of the signal which conveys meaningful information related to a subject's physical, physiological or cortical activity, level of consciousness, sleep stage, occurrence of a seizure, level of sedation and the like. Fourth, the system should preferably include outputs which result in visual and/or audible feedback capable of informing the user of the state of the patient related to quantification of physical, physiological or cortical activity, level of consciousness, sleep stage, occurrence of a seizure, level of sedation and the like at any time during the period of time that the system is monitoring the patient.

Preferably, the system should operate in real time. One example of real-time operation is the ability of the system to detect a seizure or brain dysfunction event as it is happening, rather than being limited to analysis that takes place minutes or hours afterward.

The processor or computer, and the methods of the present invention preferably contain software or embedded algorithms or steps that automatically identify artifacts and even more preferably remove the artifacts from the physiological or other sensor signal, and automatically quantify physical, physiological or cortical activity, level of consciousness, sleep stage, identify seizures or other brain dysfunction, level of sedation based on the essentially artifact free EEG signal.

The system described in this invention also preferably incorporates a number of unique features that improve safety, performance, durability, and reliability. The system should preferably be cardiac defibrillator proof, meaning that its electrical components are capable of withstanding the surge of electrical current associated with the application of a cardiac defibrillator shock to a patient being monitored by the system, and that the system remains operable after sustaining such a surge. The system should preferably have shielded leads so as to reduce as much as possible the effects of external electromagnetic interference on the collection of biopotential or physiological signals from the patient being monitored by the system. The system should preferably be auto-calibrating, and more preferably capable of compensating for the potential differences in the gains of the input channels to the patient module. The system should preferably be capable of performing a continuous impedance check on its electrode leads to ensure the quality of monitored signals.

Optionally, the system or monitor may be calibrated or tested via the utilization of a "virtual patient" device, which outputs pre-recorded digital EEG in analog format and in real time in a manner similar to what would be acquired from an actual patient, possibly with data from patients with known brain dysfunction or brain wave abnormalities. This virtual patient can also output any arbitrary waveforms at amplitudes similar to those of EEG signals. These waveforms may be used for further testing of the amplification system, such as for the determination of the amplifier bandwidth, noise profile, linearity, common mode rejection ratio, or other input requirements.

In substantially all embodiments, the invention utilizes at least two separate measures which provide at least probabilities of true and false artifacts in physiological signals, particularly in EEG signals. These measures are preferably artifact detection methods, processes or algorithms, preferably at least one of which is a method, process or algorithm for sensitivity and at least one of which is for specificity. Sensitivity methods, processes or algorithms are those that are designed to be or happen to be more accurate and useful for the detection and/or calculation of the presence and/or probability of the presence of real artifacts in an EEG, other physiological signal or other sensor signal. Specificity methods, processes or algorithms are those that are designed or happen to be more accurate and useful for the detection and/or calculation of the absence and/or probability of the absence of artifacts, in an EEG, other physiological signal, or other sensor signal. Another way to describe these two types of methods, processes or algorithms is that those for sensitivity test for the percentage of accurate detections when presented with true artifacts whereas those for specificity test for the percentage of accurate non-detections when presented with a signal with no artifacts. Each embodiment of the present invention utilizes a combination of at least one of each type of detection method in order to maximize the accuracy and reliability of the detection process and ensure that when an artifact is detected it truly is present and can be removed without corrupting or compromising the underlying EEG, other physiological signal or other sensor signal. Otherwise, the portion of the signal that contains the artifact can be removed from analysis.

A major benefit of utilizing at least one sensitivity and at least one specificity method, process or algorithm in all embodiments is that it provides a two-tier artifact detection process whereas most systems for artifact detection only contain methods for detecting the presence of artifacts. Generally, sensitivity algorithms utilize thresholds to determine whether an artifact is present. With the present invention, sensitivity thresholds are used to detect the presence of artifacts, and can be set lower, which allows the invention to detect more artifacts than most other systems. However, setting a lower sensitivity threshold does sometimes lead to the system detecting artifacts that are not actually present. The present invention counteracts this problem of false artifact detection with the addition of the specificity methods, processes or algorithms which detect normal waveforms, or the absence of artifacts. Using this two-tiered artifact detection system, the present invention allows for increased identification of and accuracy in detection of real artifacts as well as security against false identification of artifacts by using the specificity methods, processes or algorithms to verify whether artifactual portions of the waveform actually contain the artifacts identified. Following are some examples of embodiments of the present invention utilizing this combination of artifact detection techniques.

One embodiment of the present invention is a method of for monitoring a patient under anesthesia comprising the steps of acquiring an EEG signal from a patient, analyzing with a processor the EEG signal at substantially the same time as the signal is acquired with at least two separate measures, the two separate measures at least providing probabilities of the presence or absence of artifacts in the EEG signal, combining the two separate measures of the probabilities of the presence or absence of artifacts to detect or remove the artifacts, and analyzing the EEG signal containing the detected or removed artifacts using a cortical activity measure.

Another embodiment of the present invention is a method of monitoring a patient under anesthesia comprising the steps of acquiring an EEG signal from a patient, analyzing with a processor the EEG signal at substantially the same time as the signal is acquired with at least two separate measures, the two separate measures at least providing probabilities of the presence or absence of artifacts in the EEG signal, combining the at least two separate measures of the probabilities of the presence or absence of artifacts to detect or remove the artifacts, analyzing the EEG signal containing the detected or removed artifacts using a cortical activity measure, and outputting a signal based at least in part on the cortical activity measure to a device for communicating the outputted signal a clinician monitoring the patient under anesthesia.

Still another embodiment of the present invention is a method of for monitoring a patient under anesthesia comprising the steps of acquiring an EEG signal from a patient; analyzing with a processor the EEG signal at substantially the same time as the signal is acquired with at least two separate measures, the two separate measures at least providing probabilities of the presence or absence of artifacts in the EEG signal, combining the two separate measures of the probabilities of the presence or absence of artifacts to detect or remove the artifacts, analyzing the EEG signal containing the detected or removed artifacts using a cortical activity measure, and outputting a signal based at least in part on the cortical activity measure to a device for controlling the patients level of anesthesia.

Yet another embodiment of the present invention is a method of detecting seizure in a subject comprising the steps of acquiring an EEG signal from a subject who may be having a seizure(s); analyzing with a processor the EEG signal at substantially the same time as the signal is acquired with at least two separate measures, the two separate measures at least providing probabilities of the presence or absence of artifacts in the EEG signal, combining the two separate measures of the probabilities of the presence or absence of artifacts to detect or remove the artifacts, and analyzing the EEG signal containing the detected or removed artifacts using a seizure detection measure.

Yet another embodiment of the present invention is a method of detecting seizure in a subject comprising the steps of acquiring an EEG signal from a subject who may be having a seizure(s); analyzing with a processor the EEG signal at substantially the same time as the signal is acquired with at least two separate measures, the two separate measures at least providing probabilities of the presence or absence of artifacts in the EEG signal, combining the two separate measures of the probabilities of the presence or absence of artifacts to detect or remove the artifacts, analyzing the EEG signal containing the detected or removed artifacts using a seizure detection measure, and outputting a signal based at least in part on the seizure detection measure to a device for communicating the outputted signal to a caregiver monitoring the subject.

Yet another embodiment of the present invention is method of detecting or removing artifacts in a physiological signal comprising the steps of acquiring a physiological signal from a subject, analyzing with a processor the physiological signal at substantially the same time as the signal is acquired with at least two separate measures, the two separate measures at least providing probabilities of the presence or absence of artifacts in the physiological signal and combining the two separate measures of the probabilities of the presence or absence of artifacts to detect or remove the artifacts.

Yet another embodiment of the present invention is a method of detecting or removing artifacts in a physiological signal comprising the steps of instructing a subject to perform an artifact generating routine while acquiring a reference physiological signal from the subject, training an artifact detector using the reference physiological signal, acquiring a diagnostic physiological signal from a subject, analyzing with a processor the diagnostic physiological signal at substantially the same time as the signal is acquired with the trained artifact detector comprising at least two separate measures, the two separate measures at least providing probabilities of the presence or absence of artifacts in the physiological signal, and combining the two separate measures of the probabilities of the presence or absence of artifacts to detect or remove the artifacts from the physiological signal.

Yet another embodiment of the present invention is a method of detecting or removing artifacts in a physiological signal comprising the steps of training an artifact detector using data from a reference subject(s) using known artifacts, acquiring a physiological signal from a subject, analyzing with a processor the physiological signal at substantially the same time as the signal is acquired with the trained artifact detector comprising at least three separate measures, the three separate measures at least providing probabilities of the existence of artifacts in the signal, probabilities of the absence of artifacts from the signal and of normalization of an amplitude in the physiological signal, and combining the three separate measures of the probabilities of the presence of artifacts, absence of artifacts and normalization of the amplitude to detect or remove the artifacts.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention and together with the description serve to explain the principles and operation of the invention.

DETAILED DESCRIPTION OF THE DRAWINGS

Figure 1:
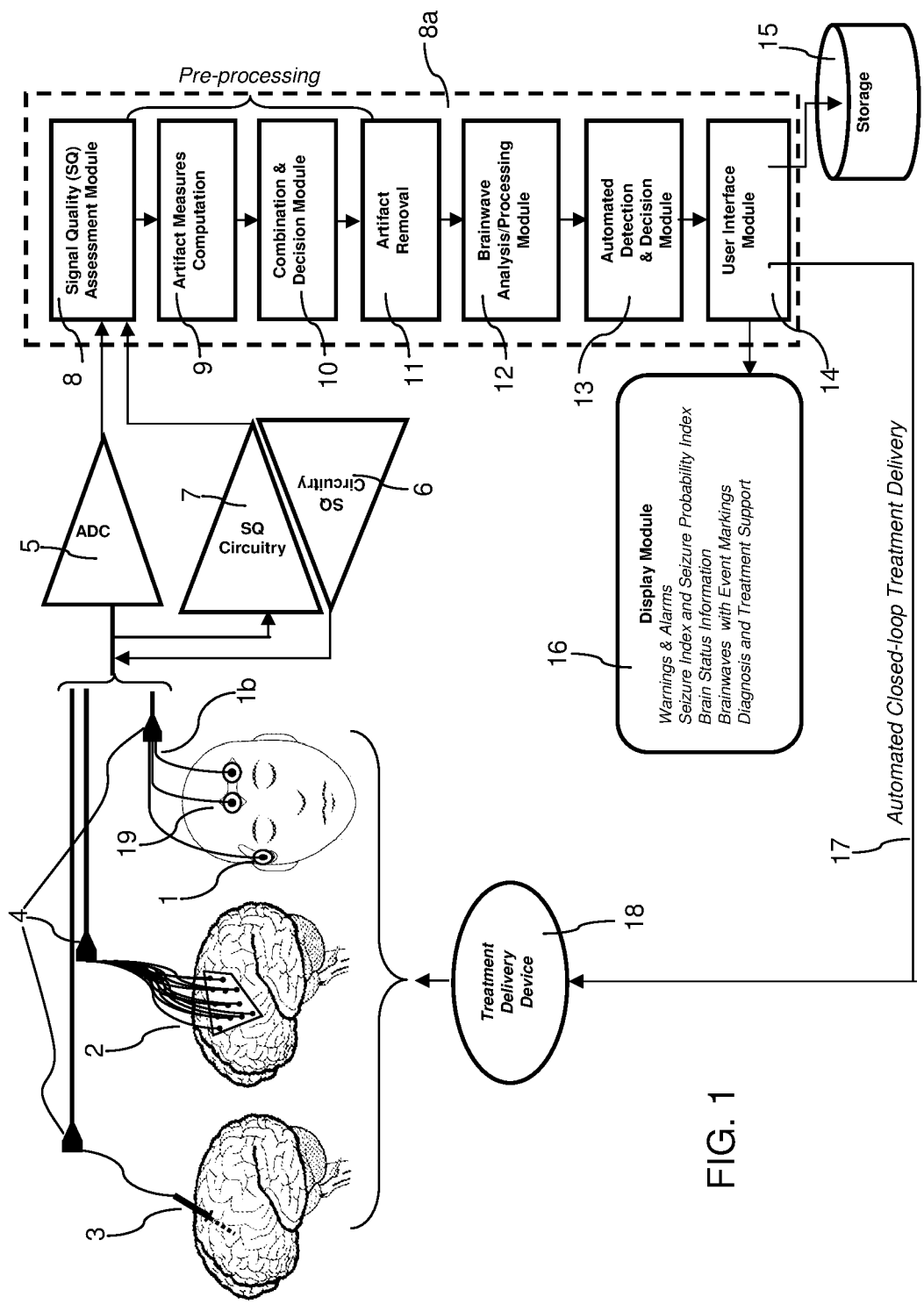
FIG. 1. Block diagram of a system overview for real-time applications.

The present invention relates to a physiological monitor and system, more particularly to an electroencephalogram (EEG) monitor and system, and a method of detecting the presence or absence of artifacts and possibly removing artifacts from an EEG, other physiological signal or other sensor signal without corrupting or compromising the signal.

All embodiments of the present invention involve acquiring an EEG, other physiological signal or other sensor signal from a subject or a patient, the subject being any type of animal including human subjects. The precise method for acquiring a signal from the subject or patient varies according to the physiological signal being acquired and analyzed. In one most preferred embodiment, that is acquiring EEG signals, electrodes can be placed at various locations on the subject's scalp in order to detect EEG or brain wave signals. Common locations for the electrodes include frontal (F), temporal (T), parietal (P), anterior (A), central (C) and occipital (O). Preferably for the present invention, at least one electrode is placed in the frontal position. In order to obtain a good EEG or brain wave signal it is desirable to have low impedances for the electrodes. Typical EEG electrode connections may have impedance in the range of from 5 to 10 K ohms. It is in generally desirable to reduce such impedance levels to below 2 K ohms. Therefore a conductive paste or gel may be applied to the electrode to create a connection with impedance below 2 K ohms. Alternatively or in conjunction with the conductive gel, the subject's skin may be mechanically abraded, the electrode may be amplified or a dry electrode may be used. Dry physiological recording electrodes of the type described in U.S. Pat. No. 7,032,301 are herein incorporated by reference. Dry electrodes provide the advantage that there is no gel to dry out or irritate the skin, which guaranties long shelf life and longer periods of monitoring the subject, no abrading or cleaning of the skin, and that the electrode can be applied in hairy areas such as the scalp. Additionally, preferably at least two electrodes are used-one signal electrode and one reference electrode; and if further EEG or brain wave signal channels are desired, the number of electrodes required will depend on whether separate reference electrodes or a single reference electrode is used. For the various embodiments of the present invention, preferably an electrode is used and the placement of at least one of the electrodes is at or near the frontal lobe of the subject's scalp.

In other embodiments of the present invention, electrodes may be placed at specific points on the subject's body for measuring cardiac signals using an ECG. ECG is used to measure the rate and regularity of heartbeats, the size and position of the chambers, any damage to the heart, and in diagnosing sleeping disorders. As the heart undergoes depolarization and repolarization, electrical currents spread throughout the body because the body acts as a volume conductor. The electrical currents generated by the heart are commonly measured by an array of preferably 12 electrodes, placed on the body surface. Although a full ECG test usually involves twelve electrodes, only two are required for many tests such as a sleep study. These are placed on the subject's left-hand ribcage, under the armpit and on the right-hand shoulder, near the clavicle bone. An ECG is important as a tool to detect the cardiac abnormalities that can be associated with respiratory-related disorders. Preferably electrodes are placed on each arm and leg, and six electrodes are placed at defined locations on the chest. The specific location of each electrode on a subject's body is well known to those skilled in the art and varies amongst individual and different types of subjects. These electrode leads are connected to a device contained in the signal processing module of the present invention that measures potential differences between selected electrodes to produce electrocardiogramacings.

Other similar methods of acquiring physiological signals with which the present invention are known to those skilled in the art for acquiring other signals such as electrical impedance tomography (EIT), electromyography (EMG) and electro-oculography (EOG).

In some embodiments, an EEG signal is measured from a subject or patient who may be having a seizure(s). Similar to above, the patient is attached to an EEG/seizure monitoring system via some form of electrodes and electrode leads. Particularly if the patient is known to be in danger of having a seizure, the EEG signal can be analyzed watching for waveforms that are indicative of the patient having a seizure so proper medical care can be given.

Other sensor signals measuring physical conditions of the subject include blood pressure measurements, galvanic skin response, respiratory effort, respiratory flow, body movement, pulse oximetry, and the like.

One step involves instructing a subject to perform an artifact generating routine while acquiring a physical or physiological reference signal from the subject. Preferably, this is a physiological reference signal and further is an EEG signal. This is the first step in the optimization or calibration technique option for use of the system that utilizes a reference signal created from the particular patient. This process allows a clinician to produce a reference signal from the particular patient or subject that is used to optimize or calibrate the artifact detector system's sensitivity and specificity algorithms to more accurately detect the presence and absence of artifacts in that particular patient or subject's EEG, other physiological signal or sensor signal. Once the patient is attached to the system via some form of electrodes and leads described above, a clinician gives the patient or subject instructions (e.g., blink your eye(s), raise your eyebrow(s), bite down, etc.) in order to produce known, identifiable artifacts which are manifested in the resultant EEG, other physiological signal or sensor signal output to the clinician or user.

Another step involves training an artifact detector using a reference EEG signal. This step is one option for optimizing and calibrating the system of the present invention for accuracy in the detection of the presence or absence of artifacts and removal of artifacts from the EEG, other physiological signal or sensor signal that utilizes the controlled artifact reference signal from the particular patient. The signal produced above by giving the patient or subject instructions in order to produce controlled artifacts, and which therefore contains such known artifacts is then analyzed using the system containing the present invention to detect the presence of those artifacts created and absence of others not expected to have been created. The results of the artifact detection method(s) are then compared against the expected results from the known artifact generation instructions. As necessary, the process is repeated until the methods, algorithms or processes produce results that match those expected and each individual method, process or algorithm is assigned a weight based on its accuracy in detecting the various artifacts relative each other method, algorithm or process.

Another option for training the detector is using data from a reference subject(s) using known artifacts. This is another option for optimizing and calibrating the system and present invention for accuracy in the detection of the presence or absence of artifacts from the EEG, other physiological signal or sensor signal. Whereas the optimization method above utilizes controlled artifact creating from the particular patient or subject, this method utilizes a reference physiological signal containing artifacts from a database of EEG, other physiological signal or sensor signals. The reference signal is initially analyzed using the system with the present invention to detect the presence of those artifacts that are known to be present as well as the absence of artifacts that are known to be absent from the signal. The same reference signal is presented to an expert in analyzing the particular type of signal, and that expert determines where the artifacts in the signal are located and annotates it accordingly. The results from the methods, algorithms or processes within the present invention are compared against the expert annotation for accuracy and weights are assigned to each individual method, algorithm or process according to their accuracy in detecting the presence or absence of artifacts in the signal.

Although the preferred embodiment of the present invention involves the combination of artifact detection methods, algorithms or processes using a weighting method (which is a linear combination of the weights assigned to each method, process or algorithm) for optimization, other optimization techniques are available and could be utilized within the present invention. Examples of such other optimization techniques include: polling methods, decision tree methods, neural network methods, heuristic methods, and many others. Polling methods involve actively sampling the outputs of the methods, processes or algorithms to determine how accurately they are detecting the presence of artifacts or normal waveforms and using those results to assign weights to each method, process or algorithm. Decision tree methods involve creating a virtual decision tree where the presence of an artifact is the dependent variable, the value of which determines the potential outcome of each branch of the tree. These types of optimization methods are commonly used for machine learning techniques such as the optimization utilized here. Decision tree methods utilize the relationships between variables and the predicted values of those variables to determine how the system should handle each conceivable circumstance. For the purposes of the present invention, the outcome of each artifact detection method, process or algorithm is a variable, and the possible values of each are some form of true or false, most preferably mathematical for automated computer analysis, more preferably binary. Neural network methods are another type of non-linear decision method and involve a complex network of individual processing elements that create a complex network of decision modules that are determined by the individual outputs of the small scale decision elements. Neural networks are particularly useful with methods, processes or algorithms such as utilized in the present invention designed to assign weights to the outputs to produce a desired overall result. In the present case, the individual results are the outputs of each artifact detection method, process or algorithm, and the neural network would utilize each of those outputs in conjunction with each other to determine the weight that should be applied to each. This is done through the neural network model learning the relationships between the inputs and outputs of the system through training. The learning process involves repeatedly taking the observations from each individual result and comparing them against the optimal solution until the values of each of the variables is optimized with respect to each other and the overall result is as accurate and optimized as possible. Heuristic methods are experience based techniques that seek out the best possible or optimized solution.

Still another step includes acquiring a diagnostic EEG signal from a subject. Similar to the description above for obtaining an EEG (in one preferred embodiment), other physiological signal, or other physical sensor signal from the patient or subject, an EEG signal is obtained from the subject's brain by connecting the signal collection system to the patient's head utilizing scalp surface mounted electrodes, or through direct attachment to the brain by means of either intra-cranial cortical grids or implanted deep brain electrodes. Brainwave signals are transferred from the particular electrode type used, through electrode leads and into the system where they are filtered and analyzed for the presence or absence of artifacts by the system containing the present invention. Yet another step includes analyzing with a processor the EEG signal at substantially the same time as the signal is acquired with at least two separate measures, the two or more separate measures at least providing probabilities of the presence and absence of artifacts in the EEG signal. This refers to the fact that the system should preferably be able to obtain an EEG, other physiological signal or sensor signal, perform the necessary pre-processing functions (various filtering methods, analog-to-digital conversion, etc.) and run at least two artifact detection methods, algorithms or processes in real-time to essentially eliminate any lag or delay in the processing for rapid, accurate results. The system will preferably perform all these functions within an amount of time that appears to be instantaneous to the user.

Yet another step involves analyzing with a processor the diagnostic EEG signal at substantially the same time as the signal is acquired with the trained artifact detector comprising at least two separate measures, the two or more separate measures at least providing probabilities of the presence and absence of artifacts in the EEG signal. Similar to above, the system should preferably be able to obtain a diagnostic EEG or other diagnostic physiological signal, perform the necessary pre-processing functions (various filtering methods, analog-to-digital conversion, etc.) and run at least two artifact detection methods, algorithms or processes in real-time to essentially eliminate any lag or delay in the processing for rapid, accurate results. The system will preferably perform all these functions within an amount of time that appears to be instantaneous to the user.

Another step includes analyzing with a processor the EEG signal at substantially the same time as the signal is acquired with the trained artifact detector comprising at least three separate measures, the three or more separate measures at least providing probabilities of the presence of artifacts, of the absence of artifacts, and of normalization of amplitude in the EEG signal. Again, similar to above, the system should preferably be able to obtain a diagnostic EEG or other diagnostic physiological signal, perform the necessary pre-processing functions (various filtering methods, analog-to-digital conversion, etc.) and run at least three artifact detection methods, algorithms or processes in real-time to essentially eliminate any lag or delay in the processing for rapid, accurate results. The system will preferably perform all these functions within an amount of time that appears to be instantaneous to the user.

Still another step includes combining the two or more separate measures of the probabilities of the presence and absence of artifacts to detect or remove the artifacts (from the EEG signal where the separate measures are weighted when combined to optimize the detection or removal of artifacts). Each individual artifact detection method, algorithm or process produces a mathematical probability that an artifact either is present in the EEG, other physiological signal or sensor signal or is not. By weighting the results of each of these methods, algorithms or processes during the system optimization/calibration phase, the results can be combined to determine the overall likelihood that an artifact is present with much higher certainty. If the system shows that an artifact is indeed present it is more likely to be accurately showing that result and the artifact can be removed without compromising or corrupting the underlying EEG or other signal.

Another step still involves combining the three or more separate measures of the probabilities of the presence of artifacts, the absence of artifacts, and normalization of the amplitude to detect or remove the artifacts where the separate measures are weighted when combined to optimize the detection or removal of artifacts. Each individual artifact detection method, algorithm or process produces a mathematical probability that an artifact either is present in the EEG, other physiological signal or sensor signal or is not. By weighting the results of each of these methods, algorithms or processes during the system optimization/calibration phase, the results can be combined to determine the overall likelihood that an artifact is present with much higher certainty. If the system shows that an artifact is indeed present it is more likely to be accurately showing that result and the artifact can be removed without compromising or corrupting the underlying EEG or other signal.

Yet another step still includes analyzing the EEG signal containing the detected or removed artifacts using a cortical activity measure. Here the corrected (artifacts having been detected and/or removed) EEG, other physiological signal or sensor signal is analyzed by a cortical activity monitor for accurate analysis of what the patient's or subject's brain is doing.

Even still another step involves analyzing the EEG signal containing the detected or removed artifacts using a seizure detection measure. Here the corrected (artifacts detected and/or removed) EEG, other physiological signal or sensor signal is analyzed by a seizure activity monitor for accurate analysis of whether that EEG signal is indicative of the patient having a seizure.

Another step includes outputting a signal based at least in part on the cortical activity measure to a device for communicating the outputted signal to a clinician or caregiver monitoring the patient under anesthesia. Here the resulting signal with artifacts detected and removed is shown on a monitor or some other device which gives the clinician or caregiver the information regarding the patient's level of consciousness. This allows the clinician or caregiver to administer appropriate care or anesthesia medication to control the patient's consciousness as necessary.

Yet another step involves outputting a signal based at least in part in the cortical activity measure to a device for controlling the patient's level of anesthesia. Here the resulting signal with artifacts detected and removed is sent to an automated treatment delivery device which is attached to the patient to monitor his or her level of consciousness. This allows the automated treatment delivery device to administer appropriate care or anesthesia medication to control the patient's consciousness as necessary.

Still another step includes outputting a signal based at least in part on the seizure detection measure to a device for communicating the outputted signal to a clinician or caregiver monitoring the subject. The EEG signal that has been filtered through the system and has had any artifacts removed is output in any number of ways to the clinician or caregiver who is monitoring the patient, and if that signal is indicative of the patient having a seizure, that clinician or caregiver can rush to the patient's aid to administer such treatment or care as is necessary to abate the seizure and return the patient to a normal state of brain activity.

Now referring to the FIGS. 1-13, FIG. 1 is a block diagram of a system for monitoring and real-time therapy applications, and in this particular embodiment a seizure detector. The system show in FIGS. 1-13 can be adapted with modifications for other types of sensor signals described within this application. The system can be connected to the subject either on the subject's scalp 19 with mounted surface electrodes 1, intra-cranial cortical grids 2, or implanted deep brain electrode(s) 3. The electrode leads 1*b* are preferably connected to the system via a yoke 4 containing cardiac defibrillation resistors (not shown) designed to absorb the energy of a cardiac defibrillation pulse. These resistors (not shown) and the associated electronics in the front-end of the instrumentation amplifiers (not shown) are designed to protect the instrumentation electronics and in particular applications to have electromagnetic interference filters (EMF) to eliminate interference caused by other electrical devices, while still ensuring that most of the energy delivered by the pulse is used for the intended therapy. The brainwave signals are then amplified and digitized by an analog-digital converter (ADC) circuitry 5.

In addition, a signal quality (SQ) circuitry 6, 7 can be used to inject measurement currents into the leads 1*b* in order to calibrate the instrumentation amplifiers (not shown) and measure electrode impedance. Similar SQ circuitry monitors the front-end amplifiers in order to detect eventual saturation that occurs when leads 1*b* are disconnected. This information, along with the digitized brainwave signals, is relayed to the processor 8*a*.

The processor 8*a*, 25 is composed of the sub-systems 8 thru 14. The signal quality assessment module 8 is used to check whether each signal acquired by the system is of sufficient quality to be used in the subsequent analysis. This is done by continuously measuring the electrode impedance of each brainwave channel, and by quantifying the levels of 50 and 60 Hz noise in the signal. High levels of 50 or 60 Hz indicate either a poor electro-magnetic environment, or a poor connection to the patient which will result in a heightened sensitivity of the system for any other environmental noise (e.g., lead movement, vibration, etc.). High levels of 50 or 60 Hz noise are usually indicative of poor signal quality.

If the signal quality is good, the system proceeds by analyzing the acquired signals in order to detect the presence of environmental or physiological artifacts (not shown), which may be corrupting the signal. This analysis is done in the artifact measures computation module 9. With the methods or algorithms of the present invention several artifact detection methods or algorithms are used in combination. These artifact detection methods or algorithms analyze the signal for artifacts using combinations of both sensitivity and specificity methods or algorithms, each detecting the presence of artifacts in different ways, and those measures are combined to increase the accuracy of artifact detection in the combination and decision module 10. These techniques are described in greater detail in FIGS. 3 and 4. In addition methods or algorithms used in these combinations are described in FIGS. 7-13. Other artifact detection techniques may also be used in the system, devices or methods of the present invention. Some artifacts, such as ocular artifacts, can be removed from the signal by using a de-noising method. This is done at the level of the artifact detection & removal module 11.

De-noised and artifact-free signals are sent to the brainwave analysis/processing module 12. This sub-system derives information contained in the signal, such as the level of consciousness of the patient, the presence of electro-cortical silence, the level of ocular activity (EOG), the level of muscle activity (EMG), etc. This information can be used as a complement to the real-time seizure detector to provide a better diagnostic means to the user. Some of this information may also be used in the real-time seizure detector to tune properly the different thresholds used by the underlying algorithm.

The automated detection & decision module 13 is at the core of the real-time seizure detector. It uses a method that amplifies abnormal spike activity in the signal, while minimizing the background 'normal' brain activity. It also combines the real-time seizure index with the information obtained in the brainwave analysis/processing module 12 in order to provide an accurate diagnostic of the patient's brain state.

A user interface module 14 provides the means for the user to interact with the system. In the preferred embodiment, this is done through the use of a display 16, which can be a touch screen display. The display 16 is used to warn the user, in real-time, of the presence of seizures. In addition, the user interface module 14 archives all the acquired signals and processed variables into a mass storage device 15, for later review.

The mass storage device 15 is used as a long term storage archive for all of the acquired EEG signals as well as the accompanying processing results. These data will then be available for later use. The signals will then be available for historical use and review where clinicians or researchers can check for artifacts or other abnormal brain activity; for example, seizures and the like. An artifact free EEG signal can be stored in the mass storage device 15 or a corrupted signal can be stored as well with the artifacts identified as part of the signal. Furthermore, they can be used as a database from which signals can be used for baseline determination or calibration of artifact detection techniques.

Finally, in some embodiments, the system is connected to a mechanism that automatically delivers a treatment to the patient, referred in the schematic as the treatment delivery device 18. The output of the system through a processor 8*a*, 25 can be used with the treatment delivery device including a processor 8*a*, 25 in closed loop 17, partially closed loop or open loop to automatically deliver physical, electrical or chemical treatment to the subject automatically based on the occurrence of abnormal brain activity, and monitor the effectiveness of such treatment in real time.

Figure 2:
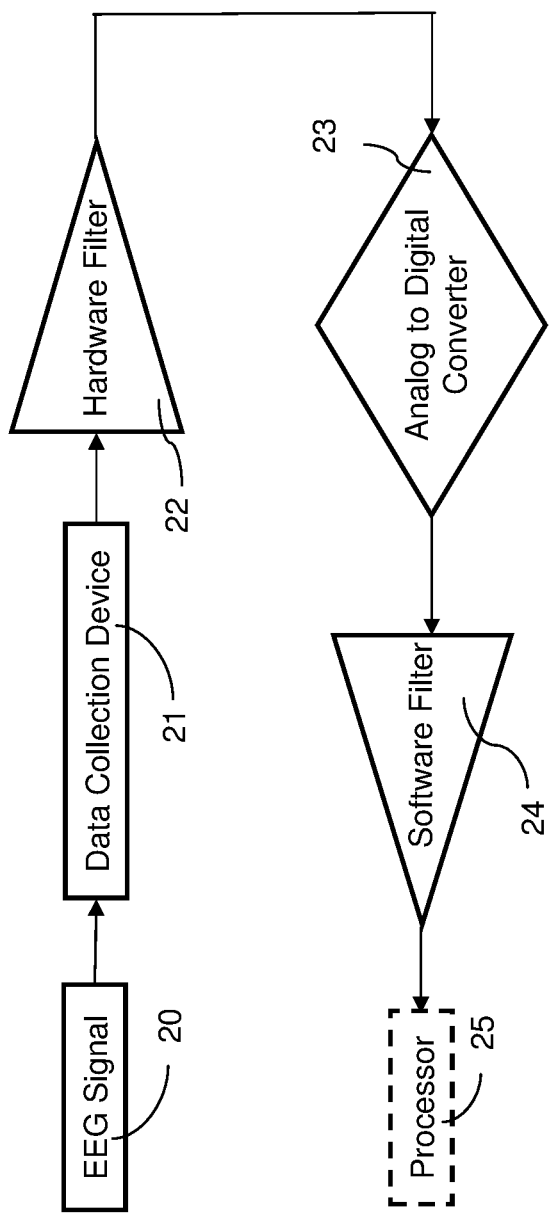
FIG. 2. Flow chart depicting the EEG signal acquisition process (leading to artifact detection processor).

FIG. 2 shows an electrical schematic of the method of one embodiment for the acquisition of an EEG signal for further processing. In this embodiment, an EEG signal is obtained via electrodes 1 and transferred to a data collection device 21, preferably at 900 samples per second (not shown). Here, the signal is run through a 0.5 Hz high pass hardware filter 22 to preferably eliminate any electromagnetic interference before being sent to an analog to digital converter 23, which converts the analog signal into its digital equivalent for further processing via software. A digital (software) filter 24 is then applied and then passes the signal to the processor 8*a*, 25 (see also FIG. 1, 8*a*), both of which modules are utilized in one or more embodiments of the present invention.

Figure 3:
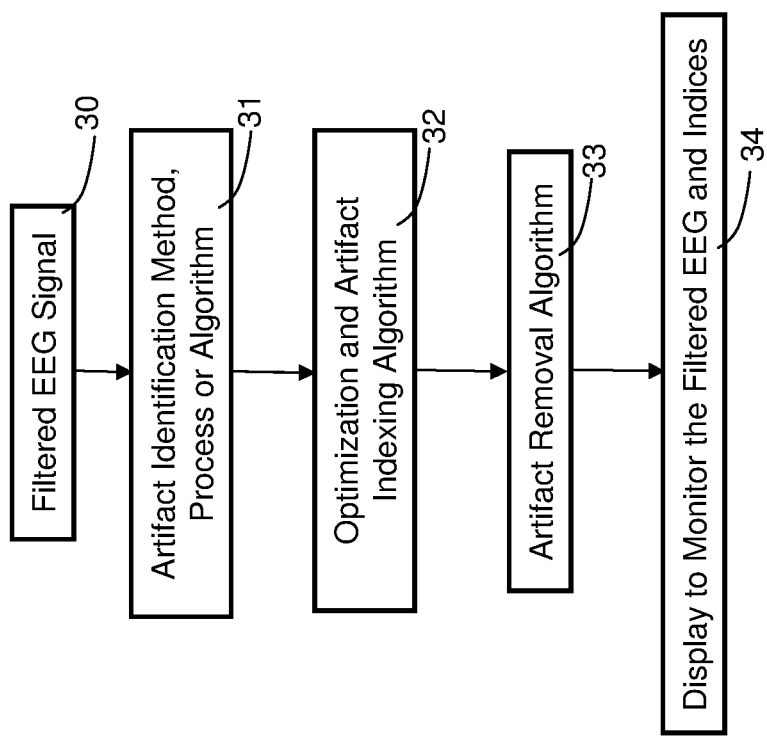
FIG. 3. Flowchart of the artifact detection process.

FIG. 3 shows a flow diagram of artifact identification and/or removal processing steps. The filtered and converted EEG signal 30 enters the processor 8*a*, 25. At least two different artifact detection and identification methods, algorithms or processes 31 are applied to the signal to determine the probability of the presence of artifacts or normal waveforms (absence of artifacts) in the EEG signal. The methods, algorithms or processes 31 are then weighted or indexed by various addition measures or steps to optimize or calibrate (See FIGS. 5 & 6) the system for accurate detection of the presence of artifacts or normal waveforms 32. Next, existing artifacts can be removed from the filtered EEG signal via an artifact removal process 33, or the entire corrupted signal can be discarded as necessary. Various additional processes (not shown) can be applied to the EEG signal to determine the subject's cortical state or if there are any abnormalities in the signal in the artifact indexing algorithm 32 before the filtered EEG signal is displayed on an output monitor 34 along with an assigned artifact index as well as an index of the subject's physiological state in real time.

Figure 4:
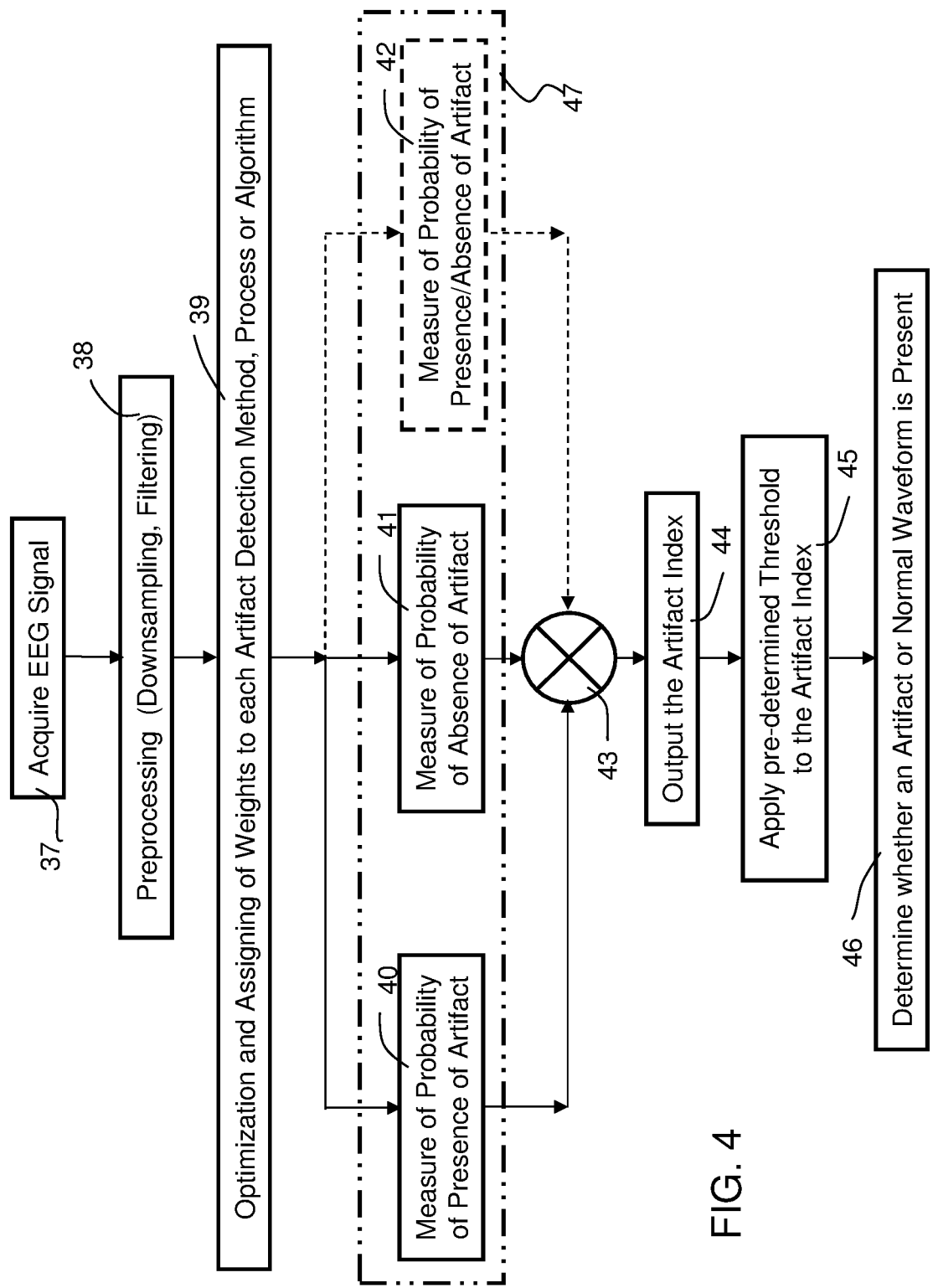
FIG. 4. Flowchart of the artifact detection process describing one embodiment of weighting and additional steps of each artifact detection and identification process.

FIG. 4 is a flow diagram presenting one embodiment of the overall process for accurate artifact identification and/or removal as well as additional steps that may be included in the detection of artifacts. An unfiltered, EEG or raw physiological or sensor signal 37 enters a series of hardware and software preprocessing algorithms and filters 38 (see FIGS. 1 & 2). This signal is then used to optimize the system and present invention 39 (explained further in FIGS. 5 & 6). Essentially, during optimization or calibration, a reference EEG, other physiological signal or sensor signal is run through the processing system and compared against expert annotation or artifacts created under controlled conditions in order to identify how accurate each individual artifact detection method, process or algorithm is at detecting a given artifact or normal waveform (absence of artifact), and then weights are assigned accordingly to each method, process or algorithm. Once the weights are assigned, the system and processor 8*a*, 25 are ready to analyze EEG, other physiological or sensor signals in real-time.

The now-filtered physiological signal encounters at least two artifact detection processes: at least one to detect the presence of artifacts 40, and at least one to detect the absence of artifacts 41. As necessary, numerous other artifact detection processes can be applied to the signal 42 to better identify both the presence and absence of artifacts thereby increasing the present invention's accuracy in determining whether an artifact is present. The artifact detection methods, processes or algorithms of the present invention are selected based on a variety of criteria. Certain methods are better in general at detecting the presence of artifacts. Others are better in general at detecting normal waveforms (the absence of artifacts). Some methods may be better at detecting the presence and/or absence of artifacts of a particular type. Still some methods may be better with particular types of physiological signals. Still other methods may be better at identifying combinations of various artifacts.

Each of the artifact detection methods, processes or algorithms calculates the probability that an artifact exists or does not exist in the given physiological signal. The weights assigned to each artifact detection process are combined 43 and an artifact index, representing the likelihood that an artifact is present, is created and output 44 to a processor 8*a*, 25. A pre-determined threshold is applied to the artifact index 45 and the determination of whether an artifact is present or not is made based on the value of the artifact index compared to the threshold value 46.

Figure 5:
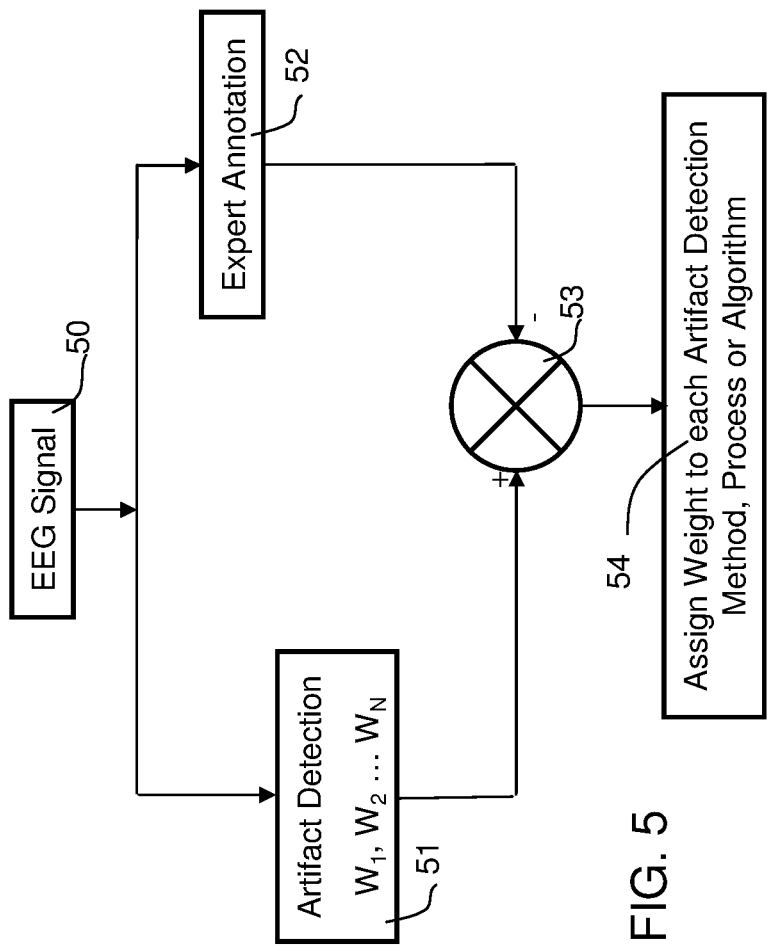
FIG. 5. Flowchart for artifact detection process detailing one embodiment of steps for error minimization using a patient database to optimize the algorithm.
Figure 6:
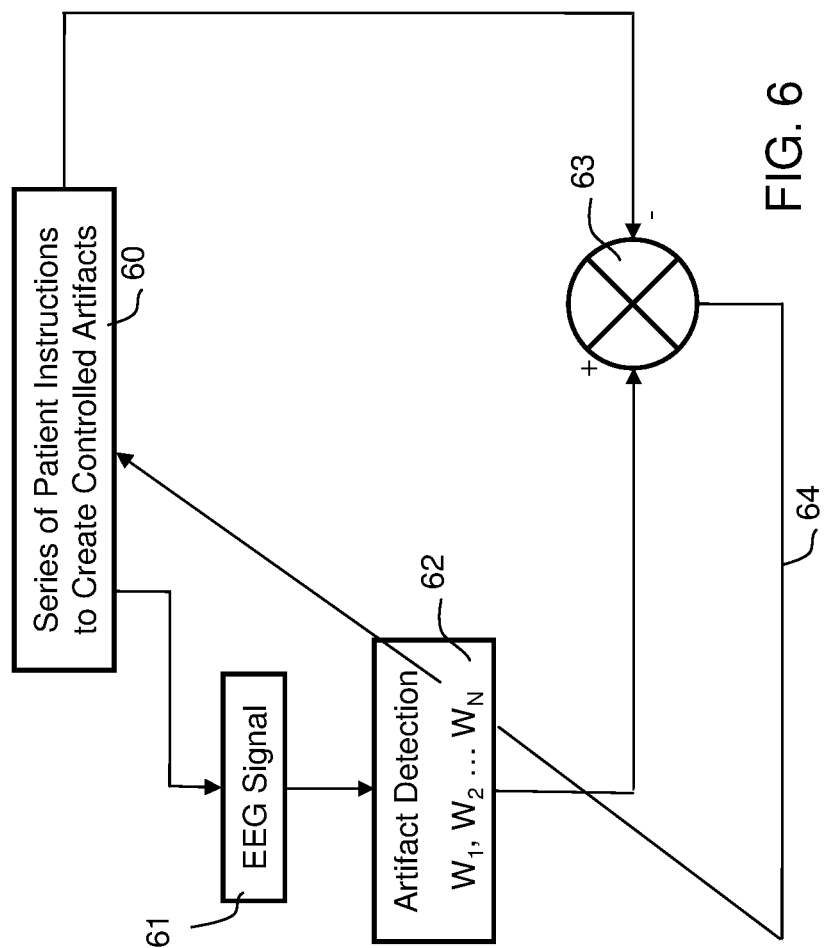
FIG. 6. Flowchart for artifact detection process detailing one embodiment of steps for error minimization using data from the specific patient acquired through a series of instructions to create controlled artifacts to optimize the algorithm.

Some of the artifact detection methods, processes or algorithms 47, which are important to the present invention, are described in more detail in FIGS. 7-13. FIGS. 5 and 6 show two embodiments of the optimization or calibration portion 39 of the processor 8*a*, 25, each embodiment utilizing a weighting technique utilized for each of methods, processes or algorithms.

FIG. 5 is a flow chart for an embodiment of artifact detection and weighting of individual artifact processes utilizing a database of patient data. The physiological signal 50 from the database is initially processed through the artifact detection measures 51 of the invention. The same physiological signal is presented to an expert who visually determines 52 whether an artifact is present. The results from these two artifact detection methods are then compared 53 and weights are assigned 54 to each of the invention's artifact detection processes according to their accuracy.

FIG. 6 is a flow chart of another embodiment of artifact detection and weighting of individual artifact processes using instructions given to the particular patient to create controlled artifacts in the EEG signal. Once the patient is attached to the monitoring system (not shown) he or she is given a set of instructions 60 for various movements designed to create known, controlled artifacts in the EEG signal 61. This signal is then processed through the artifact detection measures 62. The results of the artifact detection processes (artifact present or not) are then compared 63 against the known, expected results according to the instructions given to the patient. This entire process is repeated 64 until the invention's results match the known results of where artifacts are present, and then weights are assigned to each of the invention's artifact detection processes according to accuracy.

Figure 7:
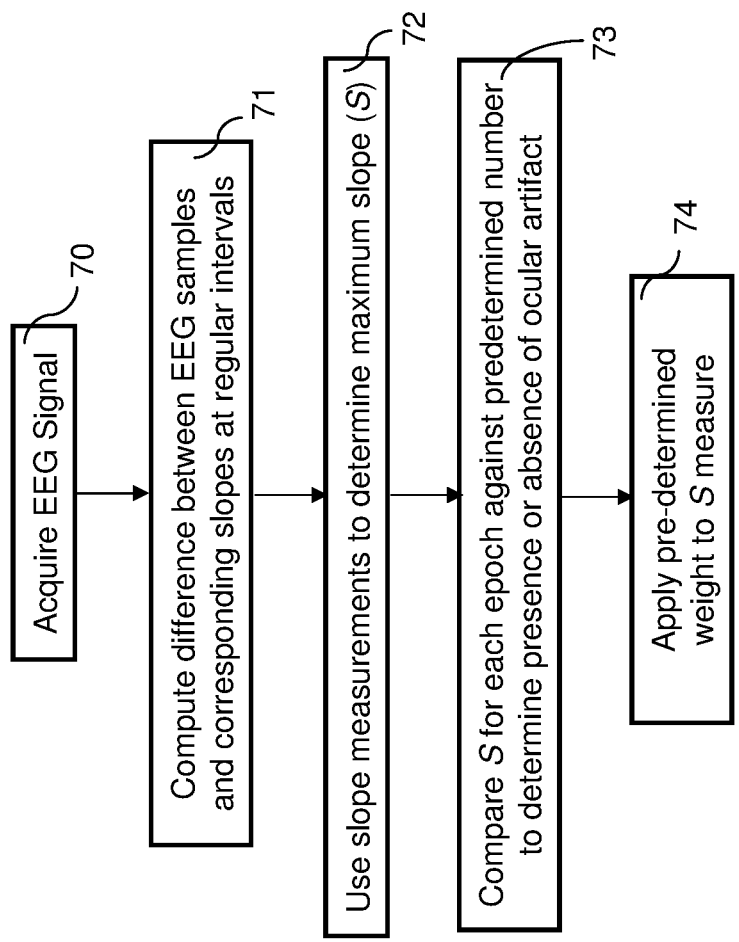
FIG. 7. Flowchart for artifact detection process detailing one embodiment of steps for detecting ocular artifacts using the maximum and minimum slopes of the EEG signal to determine probability of artifact presence.

FIG. 7 shows a flow chart describing one embodiment of the artifact detection methods, processes and algorithms that can be utilized within the present invention for detecting ocular artifacts: slope measure S. The EEG signal 70 enters the processor 8*a*, and the slopes of the EEG signal are measured and compared 71 at regular intervals. The slope measurements are then used to determine the maximum slope(S) 72 contained within the EEG signal. The maximum slope(S) for each EEG epoch is then compared against a pre-determined slope value (based on 10 randomly chosen artifact and non-artifact EEG epochs) to determine the probability that the particular epoch contains an artifact 73. The weight that was determined for this measure during the optimization process is then assigned to the value of the S measure 74.

Figure 8:
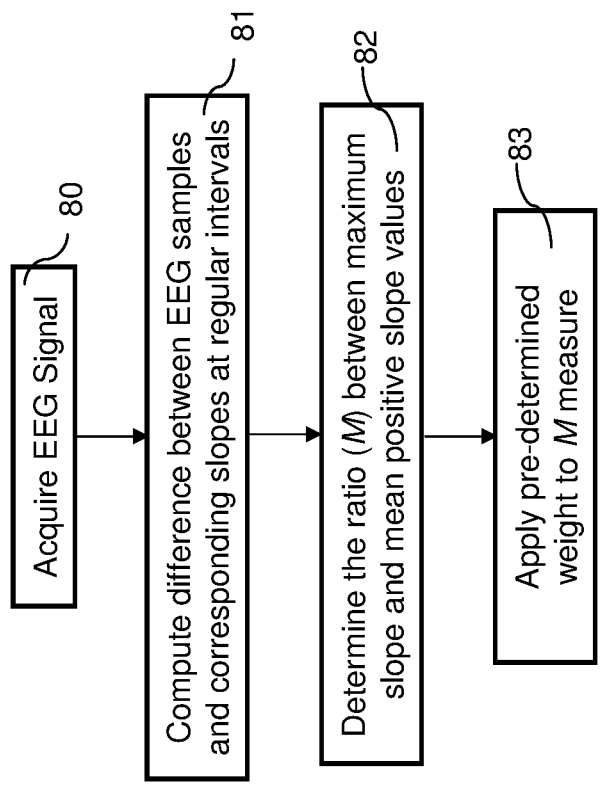
FIG. 8. Flowchart for artifact detection processing detailing an embodiment of steps for detecting measure M: a temporal measure using the "outliers" in the slope values of an EEG segment to measure the ratio of the maximum to mean slope value to determine the probability that an artifact is present.

FIG. 8 shows a flow chart describing an artifact detection process utilized within the invention for detecting artifacts: the ratio of maximum slope to mean slope, M. An EEG signal with artifacts will generally contain "outliers" in the slope values: extreme maximum or minimum values that tend to indicate artifact presence. To measure these outliers, the EEG signal 80 enters the processor 8*a*, 25 and the differences between the EEG signal and the corresponding slopes are measured and compared 81 at regular intervals. The measure M is computed 82 as the ratio between the maximum slope and the mean positive slope values of the EEG signal. This ratio M measures the variance in the EEG slope values and is utilized to determine the presence of artifacts. The weight that was determined for this measure during the optimization process is then assigned to the value of the M measure 83.

Figure 9:
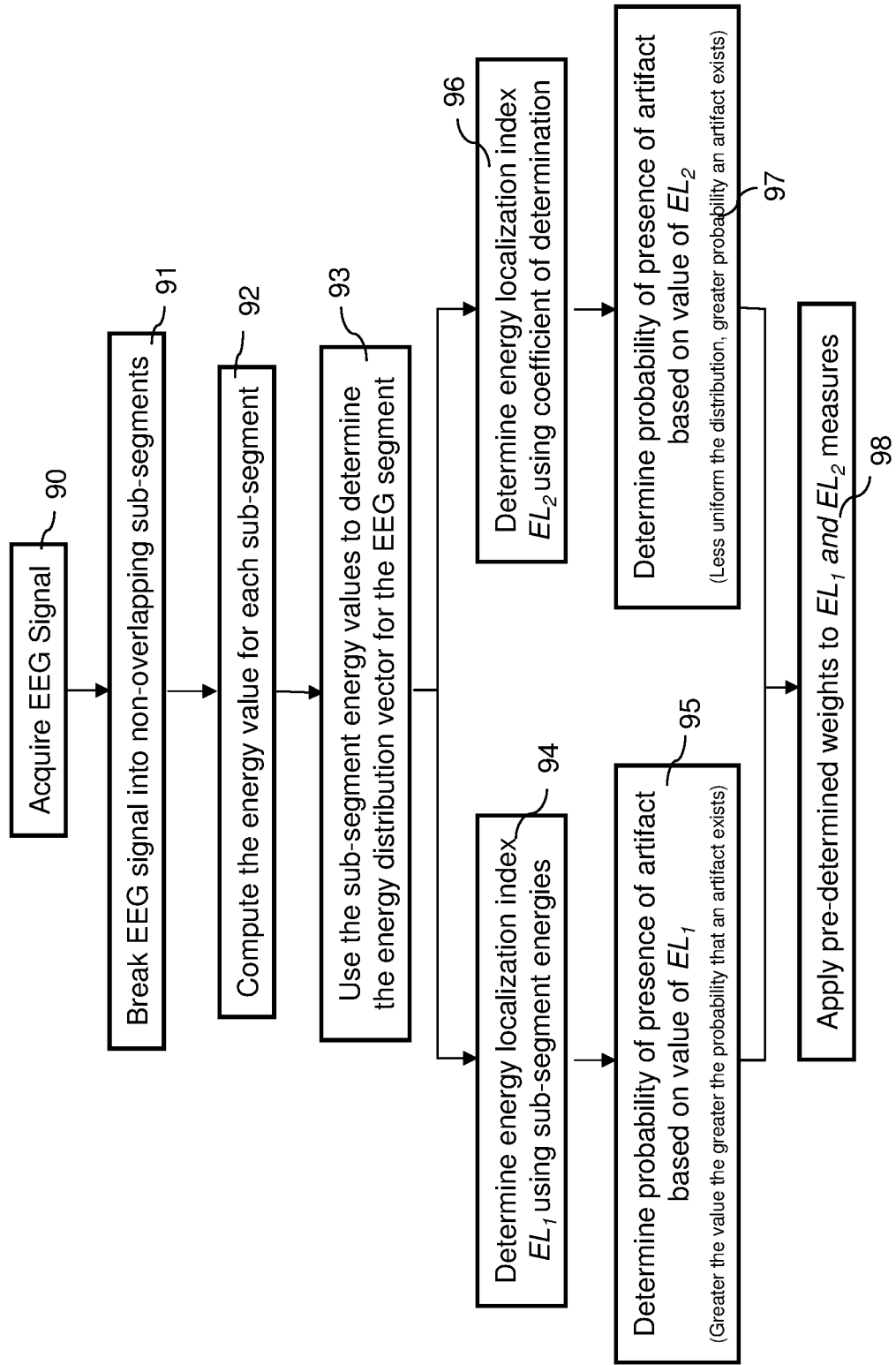
FIG. 9. Flowchart for artifact detection processing detailing another embodiment of steps for identifying $EL_1$ and $EL_2$: energy localization indices developed to detect intermittent ocular artifact waveforms in an EEG segment using the presence of high energy localized sub-segments to determine the probability of an artifact being present.

FIG. 9 is a flowchart of the artifact detection process which determines the probability of artifact presence as a function of localized energy within the EEG signal. The EEG signal 90 is captured and broken up into individual, non-overlapping sub-segments 91. The energy value for each sub-segment is calculated 92 and those values are used to create the energy distribution vector 93 representing those individual energy values for each non-overlapping sub-segment. Two separate methods are next employed to create two energy localization indices which or both calculated using the energy distribution vector calculated above.

To obtain the first energy localization index, $EL_1$, the energies of each sub-segment are used to calculate a value for $EL_1$ 94, the greater the value of which indicates a higher probability that an artifact is present in the EEG signal 95.

The second energy localization index, $EL_2$, is calculated using the coefficient of determination which accounts for the proportion of variability in the energy values of the non-overlapping sub-segments of the EEG signal. The coefficient of determination is calculated for each sub-segment 96 using the sum of the energies contain therein, and then compared to the coefficient of determination values from a uniform distribution to determine whether an artifact is present or not 97. The deviation in these values is indicative of the probability that an artifact is present in the EEG signal: the greater the deviation in the values, the greater the probability that an artifact is present. The weights that were determined for these measures during the optimization process are then assigned to the value of the $EL_1$ and $EL_2$ measures 98.

Figure 10:
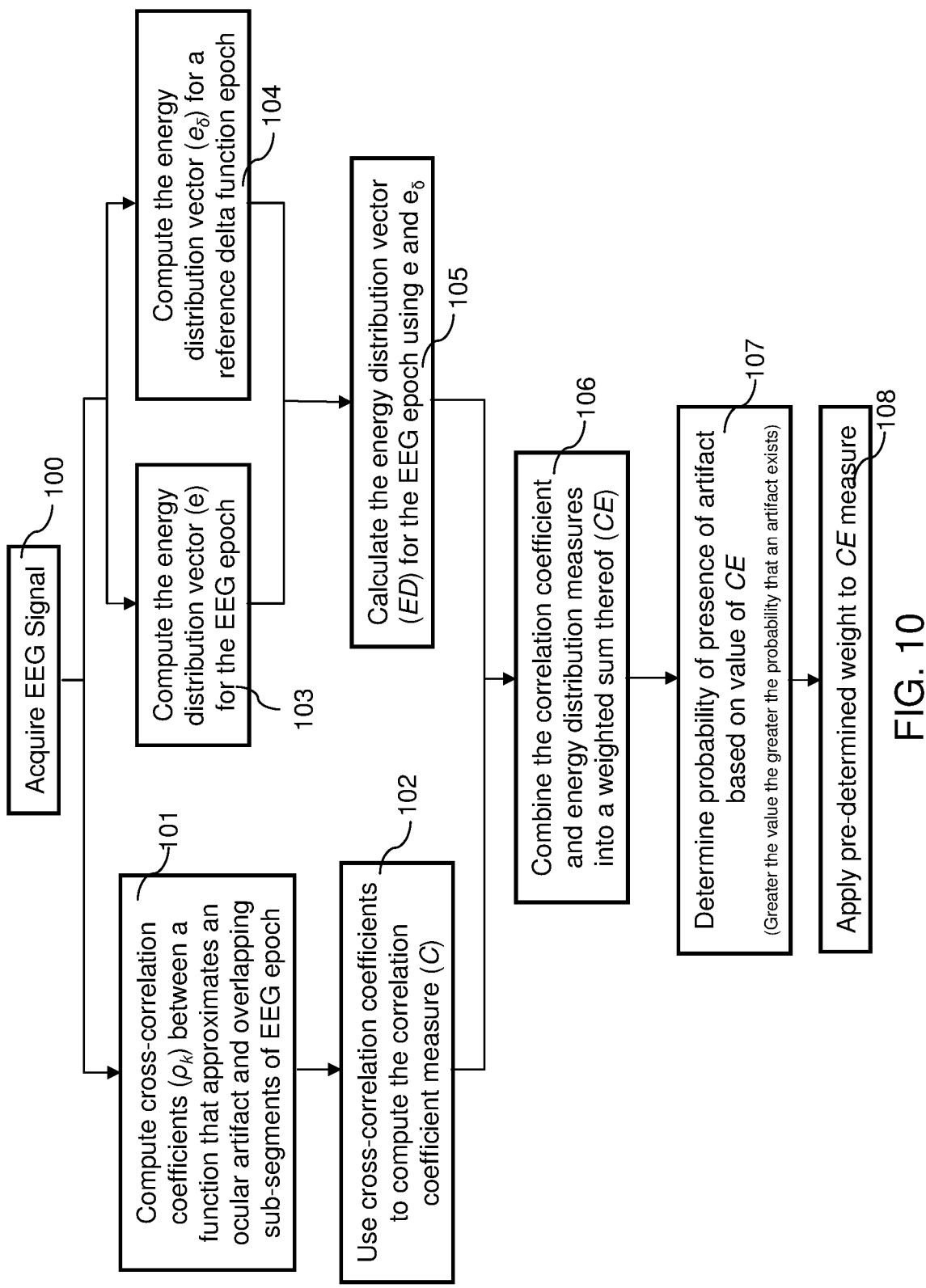
FIG. 10. Flowchart for artifact detection processing detailing another embodiment of steps for identifying CE: a combination of correlation coefficient and energy distribution measures used to calculate the probability of artifact presence.

FIG. 10 shows a flow chart describing a combined artifact detection process utilizing two separate measures, a correlation coefficient (C) and energy distribution (ED), to determine the probability that an artifact is present in a given EEG signal. An EEG signal is acquired 100 and enters the processor 8*a*, 25 where it undergoes the two separate processes used to determine the combined measure (CE) measuring the probability that an artifact is present.

For the correlation coefficient measure (C), the cross-correlation coefficients ($\rho_k$) are computed 101 between a function that approximates an ocular artifact and the overlapping sub-segments of an EEG signal. These cross-correlation coefficients are then used to calculate the correlation coefficient measure (C) 102 of the probability that an artifact exists in the given EEG signal.

To calculate the energy distribution portion of this measure, two separate energy distribution vectors are computed. First, the energy distribution vector (e) 103 for the EEG signal obtained above is computed. Simultaneously, the energy distribution vector(es) 104 for a reference delta function is computed. The overall energy distribution vector (ED) 105 is computed as a function of the two individual vectors just computed. The correlation coefficient (C) and energy distribution vector (ED) measures are combined into a weighted sum that creates the artifact detection measure (CE) 106, where the weight was chosen by using a training data set (not shown). The value of CE from the given EEG signal is then used to determine the probability that an artifact is present 107. The weight that was determined for this measure during the optimization process is then assigned to the value of the CE measure 108.

Figure 11:
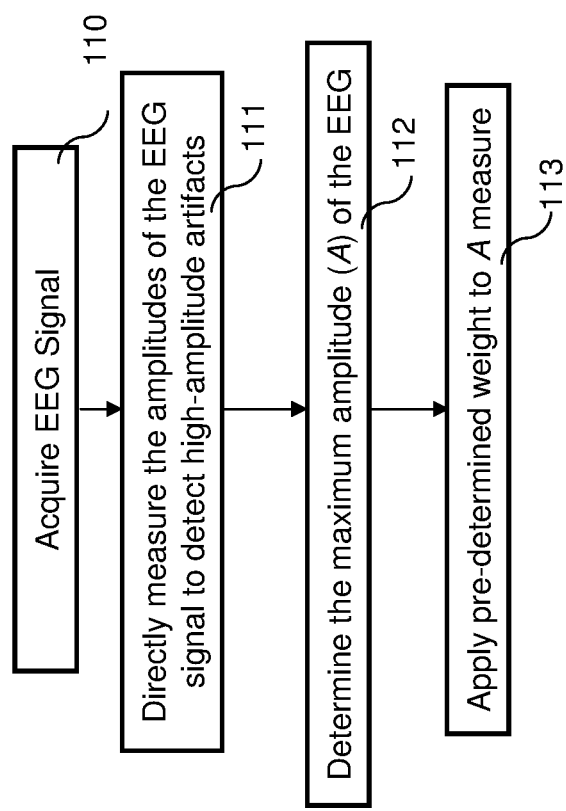
FIG. 11. Flowchart for artifact detection processing detailing another embodiment of steps for identifying A: a direct measure of high amplitude artifacts present in the EEG signal.

FIG. 11 shows a flow chart describing a direct measure for artifact detection utilizing the amplitude of the EEG signal. An EEG signal 110 is obtained enters the processor 8*a*, 25 which then directly measures the amplitudes of the EEG signal 111. The maximum amplitude (A) contained within the EEG signal is then used to determine the probability that an artifact is present 112 in the given EEG signal. The weight that was determined for this measure during the optimization process is then assigned to the value of the A measure 113.

Figure 12:
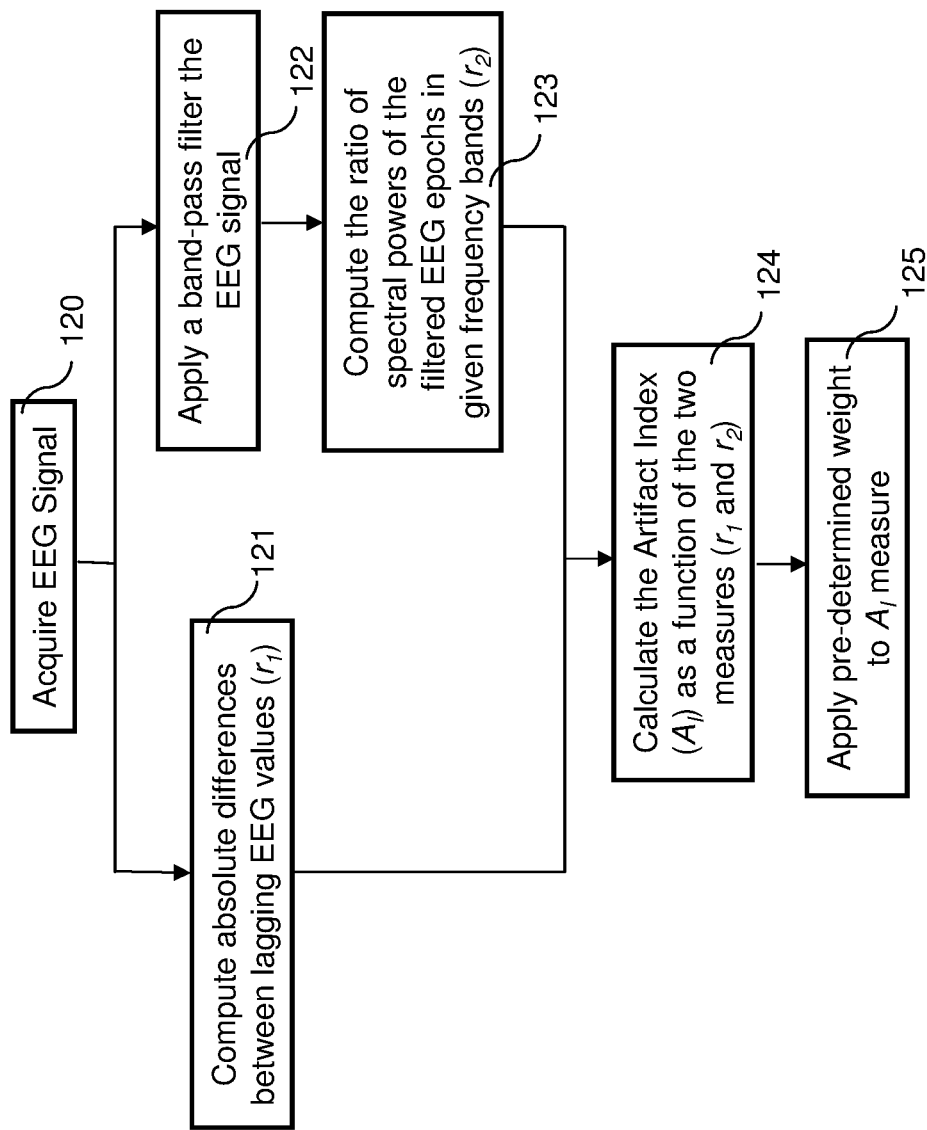
FIG. 12. Flowchart for artifact detection processing detailing another embodiment of steps for identifying Ar: a measure that tracks changes from rapid eye blinks to delta activity in frontal EEG during inducement of anesthesia by combining absolute differences between EEG signals with a ratio of spectral powers to determine the probability that an artifact is present.

FIG. 12 shows a flow chart describing the process of detecting artifacts using an artifact index ($A_1$) which is designed to track changes from rapid eye blinks to delta activity in EEG signals during induction of anesthesia. An EEG signal 120 is utilized to compute two different measures that are in turn used to calculate the artifact index ($A_1$). First, the absolute differences between lagging EEG values are determined 121 and used to calculate the measure $r_1$. For the second measure, $r_2$, a band-pass filter is applied to the EEG signal 122, and then ratio of spectral powers of this filtered EEG signal in specified frequency bands (not shown) is computed 123. The two measures, $r_1$ and $r_2$, are used to calculate the artifact index ($A_1$) 124. The weight that was determined for this measure during the optimization process is then assigned to the value of the $A_1$ measure 125.

Figure 13:
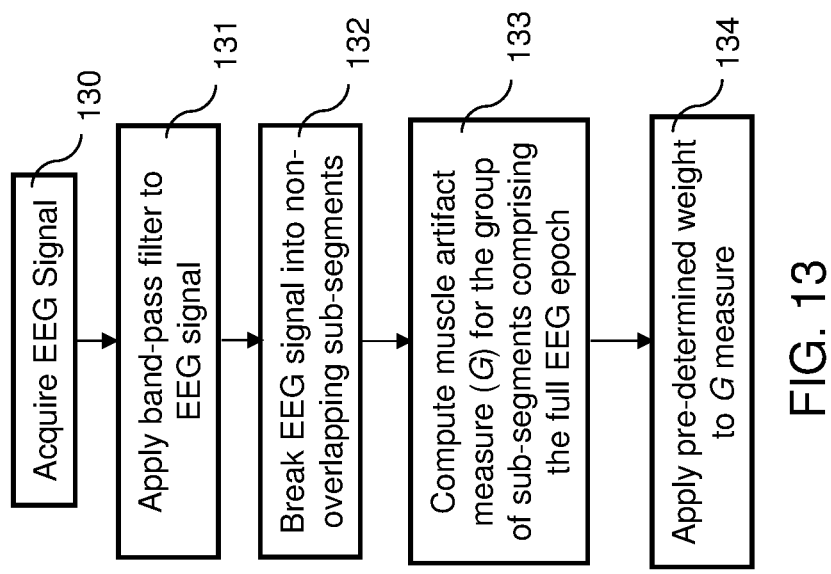
FIG. 13. Flowchart for artifact detection processing detailing another embodiment of steps for identifying G: a frequency-domain measure using high-frequency EEG activity to determine the probability of the presence of muscle artifacts.

FIG. 13 shows a flowchart of the artifact detection process utilized within the present invention for the purposes of discovering artifacts from muscle movements. An EEG signal 130 is captured and a band-pass filter 131 is applied to the signal. This filtered signal is then broken up into individual, non-overlapping sub-segments 132. The sub-sampled EEG epoch is then used to compute the muscle artifact measure, G 133, which is aimed at detecting high-frequency EEG activity which tends to indicate muscle movement artifacts within the EEG signal. The weight that was determined for this measure during the optimization process is then assigned to the value of the G measure 134.

The invention claims:

1. A treatment monitoring and delivery system to administer anesthesia medication comprising:
   a patient monitor comprising a sensor adapted for measuring an electro-encephalogram (EEG) signal from a subject; a 0.5 Hz high pass hardware filter adapted to filter the EEG signal; an analog to digital converter adapted to digitally convert the EEG signal; a processor adapted to a) analyze the EEG signal after filtering and digitizing with both a first and a second algorithms at substantially the same time as the EEG signal is acquired, the first of the algorithms adapted to measure and output the level of ocular activity (EOG) in the EEG signal, and the second algorithm adapted to determine and output electro-cortical silence from the EEG signal; and b) to combine the outputs of the first and the second algorithms to remove the EOG artifacts from the EEG signal to generate an EOG free EEG signal, the processor or a second processor module further adapted to calculate and output a level of consciousness of the subject based in part on the EOG free EEG signal;

a delivery device adapted to deliver an anesthesia treatment based on the outputted, calculated level of consciousness of the subject.

2. The system of claim 1, wherein the processor is further adapted to break the digitized EEG signal into individual non-overlapping subsegments, and an energy distribution vector is calculated for each non-overlapping sub-segment in real time.

3. The system of claim 2, the patient monitor further comprises a second sensor for measuring a second physiological signal from the subject.

4. The system of claim 1, also adapted for outputting a signal based at least in part on the calculated level of consciousness of the subject to a device for communicating the outputted signal to a clinician monitoring the patient under anesthesia.

5. The system of claim 3, wherein the second sensor measures galvanic skin response and the delivery device is adjusted/further adjusted based on the measure of galvanic skin response.

6. The system of claim 1, wherein a correlation coefficient is calculated from the EEG signal.

7. The system claim 6, wherein an energy distribution vector is calculated from the EEG signal, and the correlation coefficient and energy distribution vector are combined in a weighted sum to create an artifact detection measure.

8. A treatment monitoring and delivery system to administer anesthesia medication comprising:

a patient monitor comprising a sensor adapted for measuring an electro-encephalogram (EEG) signal from a subject; a 0.5 Hz high pass hardware filter adapted to filter the EEG signal; an analog to digital converter adapted to digitally convert the EEG signal; a processor adapted to a) analyzes the EEG signal after filtering and digitizing with both a first and a second algorithms at substantially the same time as the EEG signal is acquired, the first of the algorithms adapted to measure and output the level of ocular activity (EOG) in the EEG signal, and the second algorithm adapted to determine and output electro-cortical silence from the EEG signal; and b) to combine the outputs of the first and the second algorithms to remove the EOG artifacts from the EEG signal to generate an EOG free EEG signal, the processor or a second processor module further adapted to calculate and output a level of consciousness of the subject based in part on the EOG free EEG signal;

wherein the patient monitor is adapted to adjust an anesthesia delivery device based on the outputted, calculated level of consciousness of the subject;

wherein the patient monitor is further adapted to acquire a physiological signal from the subject while the subject is instructed to perform an artifact generating routine, and the patient monitor is trained using a reference physiological signal.

9. The system of claim 8, wherein the processor is further adapted to break the digitized EEG signal into individual non-overlapping subsegments, and an energy distribution vector is calculated for each non-overlapping sub-segment in real time.

10. The system of claim 8, the patient monitor further comprises a second sensor for measuring a second physiological signal from the subject.

11. The system of claim 9, also adapted for outputting a signal based at least in part on the calculated level of consciousness of the subject to a device for communicating the outputted signal to a clinician monitoring the patient under anesthesia.

12. The system of claim 10, wherein the second sensor measures galvanic skin response and the delivery device is adjusted/further adjusted based on the measure of galvanic skin response.

13. The system claim 8, wherein a correlation coefficient is calculated from the EEG signal.

14. The system claim 9, wherein an energy distribution vector is calculated from the EEG signal, and the correlation coefficient and energy distribution vector are combined in a weighted sum to create an artifact detection measure.

15. A treatment monitoring and delivery system to administer anesthesia medication comprising:

a patient monitor comprising a sensor adapted for measuring an electro-encephalogram (EEG) signal from a subject; a 0.5 Hz high pass hardware filter adapted to filter the EEG signal; an analog to digital converter adapted to digitally convert the EEG signal; a processor adapted to a) analyzes the EEG signal after filtering and digitizing with both a first and a second algorithms at substantially the same time as the EEG signal is acquired, the first of the algorithms adapted to measure and output the level of ocular activity (EOG) in the EEG signal, and the second algorithm adapted to determine and output electro-cortical silence from the EEG signal; and b) to combine the outputs of the first and the second algorithms to remove the EOG artifacts from the EEG signal to generate an EOG free EEG signal, the processor or a second processor module further adapted to calculate and output a level of consciousness of the subject based in part on the EOG free EEG signal;

a delivery device adapted to deliver an anesthesia treatment based on the outputted, calculated level of consciousness of the subject;

wherein the patient monitor is further adapted to be trained using data from a reference subject(s) with known artifacts.

16. The system of claim 15, wherein the processor is further adapted to break the digitized EEG signal into individual non-overlapping subsegments, and an energy distribution vector is calculated for each non-overlapping sub-segment in real time.

17. The system of claim 16, also adapted for outputting a signal based at least in part on the calculated level of consciousness of the subject to a device for communicating the outputted signal to a clinician monitoring the patient under anesthesia.

18. The system of claim 15, the patient monitor further comprising a second sensor wherein the second sensor measures galvanic skin response and the delivery device is further adjusted based on the measure of galvanic skin response.

19. The system of claim 15, wherein a correlation coefficient is calculated from the EEG signal.

20. The system of claim 19, wherein an energy distribution vector is calculated from the EEG signal, and the correlation coefficient and energy distribution vector are combined in a weighted sum to create an artifact detection measure.

* * * * *